United States Patent [19]
Aoki et al.

[11] Patent Number: 5,470,578
[45] Date of Patent: Nov. 28, 1995

[54] ANTIRHEUMATIC COMPOSITION

[75] Inventors: Shigehisa Aoki; Shinichi Iwasaki, both of Aichi; Nobuo Sugiura, Gifu; Sakaru Suzuki; Koji Kimata, both of Aichi, all of Japan

[73] Assignee: Seikagaku Kogyo Kabushiki Kaisha, Tokyo, Japan

[21] Appl. No.: 98,936

[22] Filed: Jul. 29, 1993

[30] Foreign Application Priority Data

Jul. 30, 1992 [JP] Japan ..................... 4-203558

[51] Int. Cl.$^6$ ............ A61K 37/22; A61K 9/48; A61K 31/715; C07H 5/06
[52] U.S. Cl. ............ 424/450; 424/423; 424/443; 424/449; 424/451; 424/464; 514/62; 536/55.3; 528/354; 528/361; 273/274
[58] Field of Search .............. 424/78.05, 423, 424/443, 449, 450, 451, 464; 514/54, 62; 536/55.2, 55.3; 528/354, 361; 549/273, 274

[56] References Cited

FOREIGN PATENT DOCUMENTS

| | | |
|---|---|---|
| 0466966 | 1/1992 | European Pat. Off. |
| 0493622A | 7/1992 | European Pat. Off. |
| 8702777 | 5/1987 | United Kingdom. |

OTHER PUBLICATIONS

Annals of the Rheumatic Disease, vol. 42, No. 3, Jun. 1983, pp. 254–263, Shiozawa, S. et al Immunoelectron Microscopic Demonstration of Fibronectinin Rheumuatiod Pannus and at the Cartilage–Pannus and at the Cartilage–Pannus Junction.

The Journal of Biological Chemistry, vol. 264, No. 14, May 15, 1989, pp. 8012–8018, Yamagata, M. et al, Regulation of Cell–Substrate Adhesion by Proteoglycans Immobilized on Extracellular Substrates.

Journal of Cell Science, vol. 100, No. 2, Oct. 1991, pp. 387–395, Tsukahara, T. et al, Enhanced Expression of Fibronectin by CMD/CMD Chondrocytes and its Modulation by Exogenously added Proteoglycan.

S. Shiozawa and K. Shiozawa, Scand. J. Rheumatology, Suppl., 74, 65–72 (1988).

S. Aoki et al, Arthritis and Rheumatism, 28(5), 522–528 (1985).

S. Aoki, Chubu Rheum. Assoc., 21(1), 1–13 (1990).

S. Shiozawa et al, Annals of the Rheumatic Diseases, 51, 869–873 (1992).

R. K. Strachan et al, Annals of the Rhumatic Diseases, 49, 949–951 (1990).

N. J. Zvaifler, Adv. Immunol., 16, 265–336 (1973).

Seikagaku, 62(7), 1990).

Seikagaku, 63(8), 948 (1991).

Primary Examiner—Carlos A. Azpuru
Attorney, Agent, or Firm—Sughrue, Mion, Zinn, Macpeak & Seas

[57] ABSTRACT

This invention provides an antirheumatic composition which comprises a lipid-bound glycosaminoglycan or a salt thereof as an active ingredient and a pharmaceutically acceptable carrier and has an effect to inhibit extension of pannus.

9 Claims, 5 Drawing Sheets

ANTIRHEUMATIC COMPOSITION

FIELD OF THE INVENTION

This invention relates to an antirheumatic composition which comprises a lipid-bound glycosaminoglycan as an active ingredient.

BACKGROUND OF THE INVENTION

Rheumatoid arthritis (referred to as "RA" hereinafter) is a chronic multiple inflammatory disease causing arthritis as the main lesion, and the serum and synovia collected from RA patients contain a rheumatoid factor (to be referred to as "RF" hereinafter) as an autoantibody which reacts with immunoglobulin IgG. It seems that an abnormal immunity is concerned in morbidity in RA in view of the presence of RF, but the cause of this disease is still unclear. Changes in morbidity in RA are divided approximately into three stages as a matter of convenience (Zvaifler N. J., Adv. *Immunol.*, 16, 265–336, (1973)). The first stage is an initial stage in which an unknown etiologic factor, namely an antigen, reaches joint synovial membrane to cause synovitis. In the second stage, chronic inflammation develops widely triggered by the synovitis, to cause, for example, new formation of microvessels under the surface layer of the synovial membrane, edema in tissues under the synovial membrane and proliferation, hypertrophy and multilayered growth of surface layer synovial cells. Also, infiltration of lymphoid follicle-like lymphocytes and plasma cell infiltration occur around microvessels. In the third stage, the inflamed synovial membrane is transformed into a slender villus (pannus) which penetrates into the joint cavity and subsequently proceeds to destruction of cartilage and bone, and finally acampsia. Since the destruction of cartilage and bone in the third stage entails clinically serious functional disorder and impedes the daily life of RA patients, the third stage is concerned in most important morbidity to be treated, in addition to the prevention of the initial stage synovitis. Mechanism of the cartilage destruction includes direct decomposition of proteoglycan through the joint surface by digestive enzymes such as proteases which are released into the RA synovia in a large quantity and destruction of cells and tissues at the junction of the synovial tissue with the articular cartilage by the synovial membrane pannus. Thus, decrease in the amount of proteoglycan can be found in the cartilage surface layer of RA patients. It is said that in the RA cases, the articular cartilage surface layer is coated with an immune complex containing a fibronectin-like substance, which makes pannus advanced. Especially, fibronectin is regarded as a factor positively concerned in the extension of pannus, because it is known as a mesenchymal cell extending factor and produced in the active RA synovial membrane in a markedly large quantity (Shiozawa S., *Scand. J. Rheu.*, Suppl.74, 56–72, 1988).

As described above, the cause of RA is still unclear, and no reliable treatment of the disease has been established. Especially, there is no drug which is effective for suppressing the extension of pannus. In addition, the drugs currently used in the treatment of RA are insufficient in their effects and have a problem of causing serious side effects. In consequence, great concern has been directed toward the development of drugs which can improve the above-mentioned various symptoms of RA.

With regard to an animal model, arthritis of a rabbit induced by sensitization with heat-killed cells of an *E. coli* strain 0:14 is characterized in that it shows symptoms which are considerably close to those of RA (Aoki, S., et al., Arthritis and Rheumatism, 28., 522–528, 1985; Aoki, S., *Chubu Rheum. Assoc.*, 21, 1–13, 1990). That is, this arthritis rabbit is excellent as an RA animal model because an RF-like substance as an autoantibody specific for IgG can be detected in its serum, in addition to articular pathosis such as multilayered growth of the synovial membrane surface layer cells, edema under the surface layer cells, small circle infiltration of lymphoid follicle, fibrinoid deposition, pannus formation and the like.

Similar RA-like symptoms can also be found in the case of arthritis induced by an antigen which is caused by sensitizing heat-killed cells of the *E. coli* strain 0:14 for several months and then directly administering the heat-killed cells into the joint cavity of the knee, in order to generate arthritis synchronously at an early stage with certainty.

The present inventors previously succeeded in synthesizing a lipid-bound glycosaminoglycan by covalently bonding glycosaminoglycan with a lipid and found that it was possessed of cell adhesion-inhibiting and metastasis-suppressing activities (JP-A-4-80201; JP-A-4-80202; JP-A-4-82836; *Seikagaku*, 62 (7), 880, 1990; and *Seikagaku*, 63 (8), 948, 1991). (The term "JP-A" as used herein means an "unexamined published Japanese patent application")

Thus, as described above, great concern has been directed toward the development of an antirheumatic drug which has excellent therapeutic effects and is free from side effects such as toxicity and the like.

SUMMARY OF THE INVENTION

An object of the present invention is to provide a novel substance useful for an antirheumatic drug which ameliorates the abovementioned various RA symptoms. Particularly, the present invention aims at providing an antirheumatic drug which has an effect to suppress extension of pannus which causes cartilage destruction, is effective in alleviating inflammation of synovial membrane and does not show toxicity and side effects.

DETAILED DESCRIPTION OF THE INVENTION

The present invention relates to an antirheumatic composition which comprises a lipid-bound glycosaminoglycan or a salt thereof as an active ingredient.

The lipid-bound glycosaminoglycan of the present invention is not restricted as long as it has a structure in which a lipid is covalently bound to a glycosaminoglycan (to be referred to as "GAG" hereinafter), but preferably a structure in which a functional group of a lipid is covalently bound to a carboxyl group (including lactone), a formyl group or a primary amino group of a GAG formed by specific cleavage of the reducing terminal pyranose ring of the GAG and subsequent chemical treatment.

A particularly preferred example of the lipid-bound GAG is a lipid-bound GAG obtained by subjecting a GAG to reduction and limited oxidation (partial oxidation) reactions thereby specifically cleaving the reducing terminal pyranose ring and forming a formyl group at the GAG reducing terminal, forming a Schiff base from the formyl group and a primary amino group of a lipid and then reducing the Schiff base. Another preferred example is a lipid-bound GAG obtained by subjecting a GAG to an oxidation reaction thereby specifically cleaving the reducing terminal pyranose ring and forming a carboxyl group at the GAG reducing terminal, subjecting the resulting product to a lactonization reaction to convert the GAG reducing terminal into a lactone structure and then allowing the lactone to react with a primary amino group of a lipid.

The present invention is described further in detail below.

The lipid-bound GAG to be used as an active ingredient of the antirheumatic composition of the present invention may be known substances as disclosed in JP-A-4-80201 and JP-A-4-80202. The present invention, however, is not particularly restricted by these substances, and any lipid-bound GAG in which a lipid is covalently bound to a GAG may be used as the active ingredient of the composition of the invention.

Preferably, the lipid-bound GAG may be obtained by covalently binding a carboxyl group (including lactone), a formyl group, a hydroxyl group or a primary amino group of a GAG or any of these groups introduced into the GAG in advance to a carboxyl group, a formyl group or a primary amino group of a lipid or any of these groups introduced into the lipid in advance via an acid amide bond (—CONH—), an ester bond or an aminoalkyl bond (—CH$_2$NH—). Particularly preferred are those formed by the following bonding reactions (1) to (3).

The groups involved in the bond may be an amino group, a carboxyl group, a formyl group or a hydroxyl group which is inherently contained in a GAG or a lipid, or may be formed by a chemical treatment of the GAG or lipid or introduced in advance into the GAG or lipid through a reaction with a spacer compound which has the above functional group as its terminal groups.

(1) an acid amide bond (—CONH—) between a carboxyl group (including lactone) of a GAG formed by cleaving reducing terminal pyranose ring followed by chemical treatment and a primary amino group of a lipid;

(2) an acid amide bond (—CONH—) between a carboxyl group of a uronic acid moiety of a GAG and a primary amino group of a lipid; or (3) an aminoalkyl bond (—CH$_2$NH—) formed by reducing a Shiff base obtained by reacting a formyl group of a GAG formed by cleaving reducing terminal pyranose ring followed by chemical treatment with a primary amino group of a lipid.

The following schematically shows typical examples of the relationship between the lipid-bound GAG and its material compounds.

(1) GAG or derivatives thereof

In the above formulae, GAG is a glycosaminoglycan and ⌇NH$_2$ represents an introduced amino group.

(2) Lipid or derivatives thereof

In the above formulae, ⌇COOH represents an introduced carboxyl group.

(3) Lipid-bound GAG

The lipid-bound GAG of the present invention can be used as a salt, preferably with an alkali metal such as sodium, potassium or the like, an alkaline earth metal such as calcium, magnesium or the like, an amine such as trialkylamine or the like, and an organic base such as pyridine or the like.

The starting GAG material may be obtained by any available means including extraction from a natural source such as an animal or the like, culturing of a microorganism or chemical or enzymatic synthesis, with typical examples including hyaluronic acid, chondroitin, chondroitin sulfate (A, C, D, E and K), chondroitin polysulfate, dermatan sulfate (chondroitin sulfate B), heparin, heparan sulfate, keratan sulfate, keratan polysulfate and the like. These GAG materials may be used in the form of usually used salt such as sodium salt. Chondroitin sulfate, dermatan sulfate and hyaluronic acid are preferably used.

Usable starting lipid materials are complex or simple lipids extracted from natural sources such as animals, plants, microorganisms and the like or those synthesized or partially hydrolyzed by chemical or enzymatic means. Grycerolipids are preferably used. Typical examples of glycerolipids include grycerophospholipids such as phosphatidylethanolamine, phosphatidylserine, phosphatidylthreonine, ethanolamine plasmalogen, serine plasmalogen, lysophosphatidylcholine, lysophosphatidylinositol and the like, and acylglycerols such as monoacylglycerol, diacylgrycerol and the like neutral lipids. Of these, particularly preferred are primary amino group-containing glycerophospholipids. Though chain length and unsaturation degree are not particularly limited, palmitoyl (hexadecanoyl) or stearoyl (octadecanoyl) is effective as the acyl group of the lipid. These lipids may be used in the form of usually used salt such as hydrochloride or acetate.

A process for producing the lipid-bound GAG to be used as the active ingredient of the composition of the present invention is not particularly limited and may be any known synthetic process such as a process disclosed in JP-A-4-80201 or JP-A-4-80202. Typical examples of the synthetic process of the present invention are described in detail below.

Limited oxidation of reducing terminal

In this process, a GAG is covalently bound to a lipid by subjecting a reducing terminal xylose, galactose, uronic acid or hexosamine moiety of the GAG to reduction and limited oxidation (partial oxidation), thereby specifically opening (cleaving) the reducing terminal pyranose ring and forming a formyl group on the GAG reducing terminal to give an aldehyde compound, allowing the formyl group of the thus obtained aldehyde compound to react with a primary amino group of the lipid to form a Schiff base and then reducing the thus formed Schiff base to form an aminoalkyl bond (—$CH_2NH$—).

Reduction of the reducing terminal sugar residue in the GAG may be carried out using a reducing agent (an alkali salt of boron hydride such as sodium borohydride, sodium cyanoborohydride or the like) in an amount of from 5 to 50 equivalents, preferably from 25 to 30 equivalents, per mole of the GAG, in an appropriate aqueous solvent (water, a borate buffer or the like) at a temperature of from 10° to 30° C., preferably from 15° to 25° C. for at least 1 hour, preferably from 3 hours to 18 hours.

The thus obtained compound is then subjected to limited oxidation to form an aldehyde compound having a formyl group specifically at the GAG reducing terminal. The oxidation reaction may be carried out using an oxidizing agent (an alkali salt of periodic acid such as sodium periodate, potassium periodate or the like) in an amount of from 1 to 10 equivalents, preferably from 3 to 6 equivalents, per mole of the GAG obtained by the above reduction step, at a temperature of from 0° to 10° C., preferably from 0° to 4° C., for at least 5 minutes, preferably from 30 minutes to 2 hours.

The thus formed aldehyde compound is then allowed to react with a primary amino group of a lipid (a phospholipid or the like such as phosphatidylethanolamine) to form a Schiff base, which may be effected by mixing the aldehyde compound dissolved in an aqueous solvent (e.g., water, a phosphate buffer or the like) or an appropriate organic solvent (e.g., dimethylformamide, dimethyl sulfoxide or the like) with the lipid dissolved in an appropriate organic solvent (e.g., chloroform, methanol or the like) and allowing the mixture to react at a temperature of from 15° to 60° C. for at least 1 hour, preferably from 5 hours to 18 hours. Reduction of the Schiff base may be effected during the reaction or after completion of the reaction using an appropriate reducing agent (e.g., an alkali salt of boron hydride such as sodium borohydride, sodium cyanoborohydride or the like).

In the production of a lipid-bound GAG in accordance with the methods described herein, a bifunctional spacer compound having a primary amino group, for example, an alkylenediamine such as ethylenediamine or the like or an amino acid such as lysine or the like, instead of the primary amino group-containing lipid, is allowed to react with the abovementioned aldehyde compound thereby forming an aminoalkyl bond (—$CH_2NH$—), and then the resulting compound is allowed to react with a lipid, for example, monoacylglyceryl dicarboxylate such as monoacylglyceryl succinate or the like, having a functional group such as a carboxyl group which can react with the other functional group such as an amino group of the above spacer compound.

Lactonization of reducing terminal

In this process, a GAG is covalently bound to a lipid by oxidizing a reducing terminal xylose, galactose, uronic acid or hexosamine moiety of the GAG to specifically oxidize the reducing terminal pyranose ring and form a carboxyl group at the GAG reducing terminal, subjecting the resulting product to lactonization reaction to convert the GAG reducing terminal into a lactone structure and then allowing the thus formed lactone to react with a primary amino group of the lipid to form an acid amide bond (—CONH—).

Oxidation of the GAG reducing terminal sugar residue may be carried out using an oxidizing agent (e.g., iodine, bromine or the like) in an amount of from 2 to 50 equivalents, preferably from 5 to 15 equivalents, per mole of the GAG, in an appropriate aqueous solvent (e.g., water, a phosphate buffer or the like) at a temperature of from 0° to 60° C., preferably from 15° to 30° C., for at least 1 hour, preferably from 3 hours to 18 hours.

After the oxidation reaction, the thus obtained compound is subjected to acid treatment to form a lactone compound in which the GAG reducing terminal is specifically lactonized, using a strongly acidic cation exchange resin such as Dowex 50 (trade name, Dow Chemical Co.), Amberlite IR 120 (trade name, Organo Co., Ltd.) or the like and/or acid including inorganic acid such as hydrochloric acid, sulfuric acid or the like or organic acid anhydride such as acetic anhydride, citric anhydride, succinic anhydride or the like.

The thus obtained lactone compound is then allowed to react with a lipid having a primary amino group (a phospholipid such as phosphatidylethanolamine or the like) by reacting the lactone compound dissloved in an appropriate aqueous solvent (e.g., water, a phosphate buffer or the like) or an appropriate organic solvent (e.g., dimethylformamide, dimethyl sulfoxide or the like) with a lipid dissolved in an appropriate organic solvent (e.g., chloroform, methanol or the like) and allowing the mixture to react at a temperature of from 5° to 80° C., preferably from 30° to 60° C., for at least 10 minutes, preferably from 1 hour to 18 hours.

Similar to the case of the limited oxidation of reducing terminal, a lipid-bound GAG may also be produced by allowing a bifunctional spacer compound having a primary amino group, instead of the primary amino group-containing lipid, to react with the abovementioned lactone compound thereby forming an acid amide bond (—CONH—), and then allowing the other functional group of the above bifunctional spacer compound to react with a functional group (a carboxyl group for example) of a lipid.

Other process

In another process, a carboxyl group in the uronic acid moiety of a GAG is bound to a primary amino group of a lipid via an acid amide bond (—CONH—).

In this process, the acid amide bond (—CONH—) may be formed using a condensing agent such as 1-ethyl-3-(3-dimethylaminopropyl)carbodiimide, dicyclohexylcarbodiimide or the like, or by reacting the GAG with an activator such as N-hydroxysuccinimide, p-nitrophenol, N-hydroxybenzotriazole or the like in the presence of the abovementioned condensing agent to convert the carboxyl group in the uronic acid moiety into an active ester and then allowing the resulting active ester to react with a lipid.

Preferably, the GAG uronic acid moiety may be subjected to the above reaction as a form of an organic solvent-soluble salt including amine salt such as triethylamine salt, tributylamine salt or the like, and the reaction may be carried out in an organic solvent such as dimethylformamide, dimethyl sulfoxide, pyridine or the like.

Typical compounds,

The following illustrates preferred examples of the lipid-bound GAG compounds to be used as the active ingredient of the antirheumatic composition of the present invention.

(1) L-(α-phosphatidyl)ethanolamine dipalmitoyl-bound hyaluronic acid (compound of lot No. 600 prepared in Reference Example 1-A below)

GAG: hyaluronic acid (cockscomb origin, molecular weight of 10,000)

Lipid: L-(α-Phosphatidyl)ethanolamine dipalmitoyl

Synthesis

Lactonization of reducing terminal [see Example 1-(2)-1 in JP-A-4-80201 or Reference Example 1-A below]

(2) L-(α-phosphatidyl)ethanolamine dipalmitoyl-bound chondroitin sulfate (compound of lot No. 602-2 prepared in Reference Example 1-A below)

and n = average 25

Materials and n = average 60

Materials

GAG: chondroitin sulfate (shark cartilage origin, molecular weight of 30,000, substance mainly containing chondroitin sulfate C)

Lipid: L-(α-phosphatidyl)ethanolamine dipalmitoyl

Synthesis

Lactonization of reducing terminal [see Example 1-(2)-2 in JP-A 4-80201 or Reference Example 1-A below]

(3) Stearoylpalmitoylphosphatidylserine-bound chondroitin sulfate (Reference Example 1-B below)

GAG: chondroitin sulfate (shark cartilage origin, molecular weight of 30,000, substance mainly containing chondroitin sulfate C )

Lipid: stearoylpalmitoylphosphatidylserine

Synthesis

Lactonization of reducing terminal [see Example 1-(3) in JP-A 4-80201 or Reference Example 1-B below]

(4) Monostearoylglyceryl-bound chondroitin sulfate and n = average 60

Materials n = average 60

Materials

GAG: chondroitin sulfate (shark cartilage origin, molecular weight of 30,000, substance mainly containing chondroitin sulfate C)

Lipid: monostearoylglyceryl succinate

Synthesis

Chondroitin sulfate whose reducing terminal has been limitedly oxidized(aldehyde formation) is allowed to react with ethylenediamine and subsequently with the above lipid (amination of reducing terminal) [see Example 2- (3 ) in JP-A 4-80201 or Reference Example 3 below].

(5) L-(α-phosphatidyl )ethanolamine dipalmitoyl-bound hyaluronic acid (compound of lot No. 300 prepared in Reference Example 2 below)

That is, a lipid-bound GAG is formulated into optional dosage forms such as liquids, solids, semi-solids and the like as pharmaceutical compositions and can be administered to patients through any optional route of administration. The composition may be administered orally or parenterally. The parenteral administration includes injection into tissue such as intravenous, intramuscular, intraarticular or subcutaneous administration or rectal administration, percutaneous application or the like.

The pharmaceutical composition can be prepared in the conventional manner by mixing the lipid-bound GAG with pharmaceutically acceptable,carriers. It may also be made into controlled drug release preparations using known techniques.

and n = average 24

Materials

GAG: hyaluronic acid (cockscomb origin, molecular weight of 10,000)

Lipid: L-(α-phosphatidyl)ethanolamine dipalmitoyl

Synthesis

Limited oxidation of reducing terminal [see Example 1-(2)-1) in JP-A 4-80202 or Reference Example 2 below]

Antirheumatic composition

The antirheumatic composition of the present invention is effective in mammals including human for the treatment or prevention of chronic multiple inflammatory diseases, especially RA, in which RF is detected in the serum and synovia.

Since lipid-bound GAG compounds are soluble in water in most cases, liquid preparations thereof can be produced easily. Especially, in order to gain full effects as an antirheumatic composition, it is preferable to administer the composition by intraarticular injection. Liquid preparations such as injections and the like may be produced by dissolving the lipid-bound GAG in distilled water for injection together, if necessary, with pH-adjusting agents (hydrochloric acid, sodium hydroxide, lactic acid, sodium lactate, disodium hydrogenphosphate, sodium dihydrogenphosphate and the like) and isotonizing agents (sodium chloride, glucose and the like), subjecting the resulting solution to sterile filtration and then filling the sterile solution into ampuls.

Alternatively, to this solution may be further added mannitol, dextrin, cyclodextrin, gelatin and the like and then the resulting solution is lyophilized in vacuo to serve as preparations for injection which are dissolved upon use. Also, emulsions for injection may be produced by adding an emulsifying agent such as lecithin, Polysorbate 80 (Atlas Co.), polyoxyethylene hydrogenated castor oil or the like to the lipid-bound GAG and emulsifying the mixture in water.

In addition, the lipid-bound GAG may be formulated into solid preparations for oral administration such as powders, granules, capsules, tablets and the like together with excipients including, for example, fillers such as lactose, starch, crystalline cellulose and the like, binders such as sucrose, hydroxypropyl cellulose and the like, disintegrating agents such as carboxymethyl cellulose and the like and lubricants such as magnesium stearate, talc and the like. Alternatively, the lipid-bound GAG may be formulated into liquid preparations for oral administration such as syrups and the like together with, for example, sweeteners such as sucrose, sorbitol and the like, water, essential oil and ethanol.

The lipid-bound GAG may also be formulated into ointments together with white petrolatum, beeswax, liquid paraffin or the like or into tapes by kneading it with an adhesive such as rosin, an alkyl acrylate polymer or the like and then spreading the mixture on a non-woven fabric such as of polyethylene.

The amounts of the lipid-bound GAG in the abovementioned compositions may vary depending on dosage forms, the administration route, the number of administration and the like, but the lipid-bound GAG may be used in general in an amount of from about 0.1 to 10% by weight when used as injections, from about 1 to 80% by weight when used as oral preparations and from about 0.1 to 10% by weight when used as external preparations.

The dose of the lipid-bound GAG cannot be specified because it varies depending on ages, symptoms, weight and the like of patients and the route of administration, but it generally ranges from 0.1 to 2,000 mg/adult once a dry or within several weeks. In the case of administration (injection) into tissues, the lipid-bound GAG may be administered preferably in a dose of from 1 to 1,000 mg once a day or once within several days. When the lipid-bound GAG is administered into joint cavities, it is necessary to adjust its dose optionally according to the size of each joint cavity to be injected. For example, in the case of a knee joint cavity, it is desirable to administer the lipid-bound GAG in a dose of from 0.1 to 100 mg, or from 0.1 to 10 ml as its solution, per adult per day or once within several weeks. In the case of oral administration, the lipid-bound GAG may be administered in a dose of from about 100 to 2,000 mg once or several times daily.

Since the lipid-bound GAG of the present invention is a compound having low toxicity, it is highly safe as a pharmaceutical composition. Acute toxicity of the lipid-bound GAG was measured in the following manner.

Four-week-old male and female Sic-ddy mice were preliminary fed for one week. When the males grew into their body weights of 23 to 30 g and the females into 20 to 25 g, they were given intraperitoneally a phosphatidylethanolamine-bound chondroitin sulfate (CS-PE) or a phosphatidylethanolamine-bound hyaluronic acid (HA-PE), both obtained in Reference Example shown below and each of which was dissolved in official physiological saline to a concentration of 5%. $LD_{50}$ was measured using 10 males and 10 females in each test group. As the results, it was found that the $LD_{50}$ of each test compound was 2,000 mg/kg or higher, thus proving the safety of the compounds as a drug.

In rheumatoid arthritis, infiltration of inflammatory synovial membrane cells into the surface layer of cartilage tissues, namely pannus, is an important morbidity. The composition of the present invention is considered to prevent the pannus generation according to action mechanism which comprises immobilizing the lipid-bound GAG of the present invention on the inflammatory cartilage surface and synovial membrane tissue, thereby inhibiting adhesion of the extending inflammatory synovial membrane cells to the joint cartilage tissues. Since no antirheumatic drug having such action mechanism has been known, the composition of the present invention can be regarded as a novel antirheumatic drug.

In addition to the above pannus-suppressing activity, the composition of the present invention can be expected to show an excellent effect as an antirheumatic drug because the lipid-bound GAG has a function to improve inflammatory symptoms of synovial membrane tissues by alleviating abnormal proliferation of synovial membrane cells, deposition of fibrin, follicle-like aggregation of lymphocytes and the like.

The lipid-bound GAG to be used as the active ingredient of the composition of the present invention inherently has extremely low toxicity. It seems that the composition of the present invention, which is especially effective when topically applied to inflamed sites, does not cause side effects in other organs.

The following examples are provided to further illustrates the present invention, which include reference examples showing the synthesis of the lipid-bound GAGs, test examples showing biological activities such as pharmacological activities of the compounds and a formulation example of a pharmaceutical composition. However, the examples are not to be construed to limit the scope of the invention.

REFERENCE EXAMPLE 1

A. Synthesis of phospholipid-bound GAG by lactonization of reducing terminal (1) Synthesis of reducing terminal-oxidized GAG A 500 mg portion of hyaluronic acid (cockscomb origin; molecular weight of about 10,000; HA1) was dissolved in 10 ml of water, and the solution was mixed with 5 ml of a methanol solution of 0.1M iodine. The mixture was allowed to react at room temperature for 6 hours. To the resulting reaction mixture was added about 5 ml of 0.1N potassium hydroxide to decolor free iodine. Potassium acetate-saturated ethanol was added to the resulting solution to form a precipitate and the precipitate was collected by filtration, washed thoroughly with ethanol and then dried under a reduced pressure. Thus, 423 mg of reducing terminal-oxidized hyaluronic acid (potassium salt) was obtained.

Then, 400 mg of the thus obtained reducing terminal-oxidized hyaluronic acid was dissolved in 10 ml of water, and the solution was passed through a column packed with 50 ml of a strongly acidic cation exchange resin (Dowex 50, $H^+$ type) over 1 hour. Thus, an aqueous solution containing 390 mg of reducing terminal-lactonized hyaluronic acid was obtained.

The thus obtained solution was neutralized with tri-n-butylamine and subsequently freeze-dried to obtain 400 mg of tri-n-butylamine salt of reducing terminal-lactonized hyaluronic acid.

Other reducing terminal-lactonized GAG compounds were prepared in accordance with the above procedure, using each of the following starting materials: chondroitin (molecular weight of about 15,000; obtained by removing sulfuric acid from whale cartilage chondroitin sulfate; CH), chondroitin sulfate (shark cartilage origin: molecular weight of about 10,000, CS (S1); molecular weight of about 30,000, CS (S3); and molecular weight of about 60,000, CS (S6)), dermatan sulfate (swine skin origin molecular weight of about 15,000; DS), heparin (swine small intestine origin; molecular weight of about 15,000; Hep) and heparan sulfate (bovine kidney origin; molecular weight of about 15,000; HS). The results are shown in Table 1 below.

TABLE 1

| GAG | Amount of material GAG used (mg) | Amount of reducing terminal-oxidized GAG formed/used (mg) | Amount of reducing terminal-lactonized GAG formed (mg) |
| --- | --- | --- | --- |
| CH | 1,000 | 823/800 | 780 |
| CS (S1) | 1,000 | 901/900 | 805 |
| CS (S3) | 1,000 | 895/800 | 850 |
| CS (S6) | 1,000 | 913/900 | 887 |
| DS | 100 | 91/90 | 96 |
| Hep | 1,000 | 902/900 | 946 |
| HS | 100 | 88/80 | 72 |

(2) Preparation of L-(α-phosphatidyl)ethanolamine dipalmitoyl-bound GAG

A 400 mg portion of tri-n-butylamine salt of reducing terminal-lactonized hyaluronic acid was dissolved in 200 ml of dimethylformamide and 27.6 mg of L-(α-phosphatidyl)ethanolamine dipalmitoyl (to be referred to as "PE" hereinafter) dissolved in chloroform was added thereto. The resulting mixture was allowed to react at 70° C. for 2 hours. After removing chloroform from the reaction mixture by distillation, an excess amount of sodium acetate was added to the residue, followed by the addition of sodium acetate-saturated ethanol to form a precipitate. The thus formed precipitate was collected by filtration and dissolved in 0.3M ammonium acetate solution. The resulting solution was applied to a hydrophobic chromatographic column (400 ml of TSK gel Phenyl Toyopearl 650M, Tosoh Corporation) for adsorption. The column was washed thoroughly with 0.3M sodium chloride aqueous solution and then elution was carried out with 30% methanol aqueous solution. The reaction product was found in the 30% methanol-eluted fraction, while unreacted starting material was found in the unadsorbed fraction and washings. The 30% methanol-eluted fraction was concentrated under a reduced pressure, desalted by dialysis and then lyophilized to obtain 36 mg of the PE-bound hyaluronic acid (lot No. 600).

Lot No. 600

PE content: 6.44%

Hyaluronic acid content: 82.37%

Various PE-bound GAG compounds other than the PE-bound hyaluronic acid were prepared using PE and the reducing terminal-lactonized compounds obtained in the above step (1) in accordance with the abovementioned procedure. The amount of the starting materials used and the amount of the desired products formed are shown in Table 2 below, and the results of the proportion of PE and GAG in the products is shown in Table 3 below.

TABLE 2

| GAG | Amount of reducing terminal-lactonized GAG used (mg) | Amount of PE used (mg) | Amount of PE-bound GAG formed (mg) |
| --- | --- | --- | --- |
| CH | 700 | 32.30 | 70.20 |
| CS (S1) | 800 | 55.40 | 88.00 |
| CS (S3) | 400 | 9.26 | 20.00 |
| CS (S6) | 800 | 9.00 | 56.20 |
| DS | 90 | 4.15 | 4.50 |
| Hep | 800 | 36.91 | 24.00 |
| HS | 70 | 3.31 | 5.74 |

TABLE 3

| GAG | Lot No. | Proportion PE (%) | GAG (%) |
| --- | --- | --- | --- |
| CH | 601 | 4.30 | 90.90 |
| CS (S1) | 602 | 6.41 | 85.17 |
| CS (S3) | 602-2 | 2.01 | 89.70 |
| CS (S6) | 602-3 | 1.08 | 92.00 |
| DS | 604 | 4.00 | 90.66 |
| Hep | 605 | 4.11 | 90.01 |
| HS | 606 | 4.22 | 88.21 |

B. Synthesis of stearoylpalmitoylphosphatidylserine-bound chondroitin sulfate by lactonization of reducing terminal A 400 mg portion of reducing terminal-lactonized chondroitin sulfate prepared in the same manner as described in Reference Example 1-A-(1) was dissolved in 200 ml of dimethylformamide and 9 mg of stearoylpalmitoylphosphatidylserine dissolved in chloroform was added thereto. The mixture was allowed to react at 70° C. for 2 hours. After removing chloroform by distillation, an excess amount of a sodium acetate solution was added to the residue to produce a sodium salt. Then, sodium acetate-saturated ethanol was added thereto and a precipitate formed was collected by filtration. The precipitate was dissolved in 0.3M sodium chloride solution and treated in accordance with the same method as described in Reference Example 1-A-(2) to obtain 20.8 mg of stearoyl-palmitoylphosphatidylserine-bound chondroitin sulfate.

Phosphorus content: 0.10%

Chondroitin sulfate content: 86.15%

REFERENCE EXAMPLE 2

Synthesis of lipid-bound GAG by limited oxidation of reducing terminal (1) Synthesis of reducing terminal-oxidized GAG A 2,000 mg portion of hyaluronic acid (cockscomb origin; molecular weight of about 10,000; HA1) was dissolved in 200 ml of 0.05M borate buffer (pH 8.3), and the solution was mixed with 182 mg of sodium borohydride. The resulting mixture was allowed to react at room temperature for 5 hours. After adjusting the pH value to 4.5 with acetic acid, ethanol was added to the resulting solution to form a precipitate. The precipitate was collected by filtration and washed with ethanol to obtain 1,800 mg of reducing terminal residue-cleaved hyaluronic acid.

Then, 1,700 mg of the thus prepared reducing terminal residue-cleaved hyaluronic acid was dissolved in 250 ml of 40 mM imidazole buffer (pH 6.5), and the solution was mixed with 139.96 mg of sodium periodate. The resulting mixture was allowed to react at 0° C. for 1 hour. Thereafter, ethanol was added to the reaction mixture to form a precipitate. The precipitate was collected by filtration and washed with ethanol to obtain 1,600 mg of reducing terminal-limitedly oxidized hyaluronic acid.

In the same manner, 897 mg of reducing terminal residue-cleaved chondroitin sulfate was obtained using 1,000 mg of chondroitin sulfate (shark cartilage origin; molecular weight of about 30,000; CS (S3)) and 31.50 mg of sodium borohydride, and 774 mg of reducing terminal residue-limitedly oxidized chondroitin sulfate was obtained using 800 mg of the reducing terminal residue-cleaved chondroitin sulfate and 22.83 mg of sodium periodate.

(2) Synthesis of L-(α-phosphatidyl)ethanolamine dipalmitoyl-bound GAG

A 1,000 mg portion of reducing terminal residue-limitedly oxidized hyaluronic acid was dissolved in 100 ml of 0.05M phosphate buffer (pH 7.0) and 69.2 ml of a chloroform-methanol mixture (2:1) containing 1 mg/ml of PE was added thereto, followed by further addition of methanol to make the mixture into a uniform solution. After the resulting solution was allowed to react at 50° C. for 1 hour, 25 mg of sodium cyanoborohydride was added to the solution and the reaction was continued at 50° C. for 2 hours. The resulting reaction mixture was concentrated under a reduced pressure and then mixed with five volumes of acetate-saturated ethanol to form a precipitate. The thus formed precipitate was collected by filtration and dissolved in 0.3M sodium chloride solution. The resulting solution was applied to a hydrophobic chromatographic column (400 ml of TSK gel Phenyl Toyopearl 650M) for adsorption. The column was washed thoroughly with 0.3M sodium chloride aqueous solution and then elution was carried out with 30% methanol aqueous solution. The desired product was found in the 30% methanol-eluted fraction, while unreacted starting material was found in the unadsorbed fraction and washings. The 30% methanol-eluted fraction was concentrated under a reduced pressure, desalted by dialysis and then lyophilized to obtain 40 mg of the PE-bound hyaluronic acid (lot No. 300).

Lot No. 300

PE content: 6.21%

Hyaluronic acid content: 62.12%

In the same manner, 29 mg of a PE-bound chondroitin sulfate (lot No. 302-2was obtained using 700 mg of the reducing terminal residue-limitedly oxidized chondroitin sulfate prepared in the above step (1), 16.15 mg of PE and 5.89 mg of sodium cyanoborohydride.

Lot No. 302-2

PE content: 2.22%

Chondroitin sulfate content: 65.52%

REFERENCE EXAMPLE 3

Synthesis of monostearoylglyceryl-bound chondroitin sulfate by amination of reducing terminal 1) Synthesis of reducing terminal-aminated chondroitin sulfate A 100 mg portion of reducing terminal-limitedly oxidized chondroitin sulfate obtained in Reference Example 2 (1) was dissolved in 50 ml of 0.05M phosphate buffer (pH 7.0), 24 mg of ethylenediamine hydrochloride was added thereto and the mixture was allowed to react at 50° C. for 30 minutes. After adding 20 mg of sodium cyanoborohydride to the mixture, the reaction was further carried out at 50° C. for 2 hours. Sodium acetate-saturated ethanol was added to the reaction mixture to form a precipitate which was collected by filtration. The precipitate was dissolved in water and desalted by dialysis. The resulting solution was allowed to be adsorbed by 50 ml of DEAE-ion exchange resin and gradient elution was carried out with a sodium chloride solution in a concentration of 0.1 to 1M. Reducing terminal-aminated chondroitin sulfate was eluted at a sodium chloride concentration of 0.4M, while free chondroitin sulfate was eluted at the concentration of 0.75M. The fraction obtained by elution with a 0.4M sodium chloride solution was desalted by dialysis and lyophilized to obtain 80 mg of reducing terminal-aminated chondroitin sulfate.

2) Preparation of gryceryl monostearate succinic acid ester

A 10.74 g of gryceryl monostearate was dissolved in 200 ml of benzene containing 3 ml of pyridine, 6 g of succinic anhydride was added thereto. The resulting mixture was refluxed for 6 houses and concentrated under reduced pressure. A precipitate formed was recrystallized from acetone to obtain 8.2 g of gryceryl monostearate succinic acid ester.

3) Preparation of active ester of gryceryl monostearate succinic acid ester

A 8 g portion of the ester obtained in the above 2) was dissolved in benzene. To the solution were added 2 g of N-hydroxysuccinic acid imide and 10 g of dicyclohexylcarbodiimide. The mixture was allowed to react at room temperature for 20 hours and then concentrated under reduced pressure. A precipitate formed was recrystallized from benzene/n-hexane to obtain 7.4 g of a desired active ester.

4) Preparation of monostearoylglyceryl-bound chondroitin sulfate

A 80 mg portion of reducing terminal-aminated chondroitin sulfate obtained in the above 1) was dissolved in 5 ml of water and 6.95 mg of the active ester obtained in the above 3) dissolved in dimethylformamide was added thereto. The resulting mixture was allowed to react at room temperature for 20 hours. Sodium acetate-saturated ethanol was added to the reaction mixture and a precipitate formed was collected by filtration. The precipitate was dissolved in a 0.3M sodium chloride aqueous solution and the resulting solution was purified in accordance with the procedure described in Reference Example 1 (2) to obtain 38 mg of monostearoylglyceryl-bound chondroitin sulfate.

Stearic acid content: 0.86%

Chondroitin sulfate content: 98.2%

TEST EXAMPLE 1

Inhibitory effect of lipid-bound GAG on extension of pannus in simultaneous organ culture of rabbit articular cartilage tissue and synovial membrane tissue (1)

Japanese white rabbits were sensitized for 7 to 8 months by intravenous injection of heat-killed *E. coli* strain 0:14, and killed cells of the same strain were injected into knee joint cavities of the sensitized rabbits to cause arthritis. After 4 to 5 weeks of the arthritis induction, the rabbits were sacrificed and dissected to aseptically collect knee articular cartilage tissues and fat tissue-containing synovial membrane tissues which were subsequently cut into 3 to 5 mm square pieces and washed with Hanks' solution.

A six-well tissue culture plate (Falcon 3046, 35 mm inside diameter, Falcon) was filled with 1 ml of Iscove's modified Dulbecco's medium (Sigma Chemical Co.) containing 10% fetal bovine serum, and a filter-equipped culture plate insert (Millicell-CM, 30 mm diameter and 0.4 μm pore size, Millipore Corp.) was soaked in the medium. A piece of the cartilage tissue prepared above was put on the filter, with the side of the joint of the piece facing upward, and then the synovial membrane tissue piece obtained above was superposed on the cartilage tissue piece in such a manner that the side of the synovial membrane cell overlapped on the joint side of the cartilage piece. Thereafter, the thus arranged tissues were incubated at 37° C.

The cartilage tissue piece was pre-treated at 37° C. for 1 hour with the PE-bound chondroitin sulfate prepared in Reference Example 1 (lot No. 602-2, to be referred to as "CS-PE" hereinafter) which had been dissolved in Hanks' solution to a concentration of 100 μg/ml prior to the incubation. Alternatively, the incubation was carried out with adding CS-PE to the medium to a concentration of 100 μg/ml. Effects of the CS-PE were then examined in the following manner.

After 4 to 8 days of the incubation, each of the resulting organ culture tissue pieces was fixed as such with a neutral formalin buffer, subjected to paraffin embedding and then sliced vertically so that the overlapping portion of the cartilage and synovial membrane could be observed. The thus obtained section was stained with hematoxylin-eosin (to be referred to as "HE" hereinafter). Microscopic observation revealed pannus-like extension of the synovial membrane cells to the cartilage tissue surface. The results were judged "++" when the cell extension was considerably strong, "+" when the extension was clearly observed, "±" when some of the synovial membrane-originated cells were found on the cartilage surface and "−" when no cell extension was found. The results are shown in Table 4.

TABLE 4

| Conditions | Degree of pannus-like extension of synovial membrane cells (n = 4) | | | |
|---|---|---|---|---|
| | 1 | 2 | 3 | 4 |
| Control (untreated) | ± | ++ | + | ++ |
| Cartilage pretreated with CS-PE 100 μg/ml | ± | ± | − | − |
| Cartilage incubated in the medium supplemented with CS-PE 100 μg/ml | + | ± | ± | ± |

As is evident from Table 4, CS-PE showed an inhibitory effect on extension of the synovial membrane cells (pannus) to the cartilage surface. The high extension inhibitory effect was obtained when CS-PE was applied to the cartilage tissue in advance (pretreated cartilage) in comparison with the case of catilage tissue incubated in the medium supplemented with CS-PE.

TEST EXAMPLE 2

Inhibitory effect of lipid-bound GAG on extension of pannus in simultaneous organ culture of rabbit articular cartilage tissue and synovial membrane tissue (2)

Japanese white rabbits were sensitized for 4 months by subcutaneous injection of heat-killed *E. coli* strain 0:14, and killed cells of the same strain were injected into knee joint cavities of the sensitized rabbits to cause arthritis. After 5 weeks of the arthritis induction, they were sacrificed and dissected to aseptically collect knee articular cartilage tissues and fat tissue-containing synovial membrane tissues which were subsequently cut into 3 to 5 mm square pieces and washed with Hank' solution. One of the thus prepared cartilage tissue pieces was added to a solution of the PE-bound chondroitin sulfate (lot No. 602-2) or the PE-bound hyaluronic acid prepared in Reference Example 1 (lot No. 600, to be referred to as "HA-PE" hereinafter), each of which had been dissolved in Hank' solution to a concentration of 100 μg/ml. The cartilage tissue pieces were pretreated at 37° C. for 1 hour and then washed again with Hank' solution.

A six-well tissue culture plate (Falcon 3046, 35 mm internal diameter, Falcon) was filled with 1 ml of Iscove's modified Dulbecco's medium (Sigma Chemical Co.) containing 10% fetal bovine serum, and a filter-equipped culture plate insert (Millicell-CM, 30 mm diameter and 0.4 μm pore size, Millipore Corp.) was soaked in the medium. A piece of the cartilage tissue pretreated with CS-PE or HA-PE and an untreated cartilage tissue piece were arranged on the filter, with the side of the joint of each piece facing upward, and then the synovial membrane tissue piece obtained above was superposed on the cartilage tissue pieces in such a manner that the side of the synovial membrane cell was overlapped on the joint side of the cartilage pieces. Thereafter, the thus arranged tissues were incubated at 37° C.

After 4 days of the incubation, the resulting organ culture tissue pieces were made into sections and subjected to HE staining in the same manner as described in Test Example 1, and pannus-like extension of the synovial membrane cells was judged in the same manner. The results are shown in Table 5.

TABLE 5

| Degree of pannus-like extension of synovial membrane cells (n = 3) | | | | | |
|---|---|---|---|---|---|
| Untreated cartilage | | | Pretreated cartilage with CS-PE | | |
| 1 | 2 | 3 | 1 | 2 | 3 |
| + | + | + | − | − | ± |
| Untreated cartilage | | | Pretreated cartilage with HA-PE | | |
| 1 | 2 | 3 | 1 | 2 | 3 |
| + | + | + | ± | + | ± |

As is evident from Table 5, pretreatment of cartilage with CS-PE, namely application of CS-PE to cartilage, is effective for inhibiting the extension of synovial membrane cells (pannus) to the cartilage surface. Pannus extension of cartilage pretreated with HA-PE also inhibited though the degree of the inhibition was not so high as CS-PE.

The lipid-bound GAG compounds prepared in Reference Examples 1 and 2 other than CS-PE and HA-PE were also examined for their effects for inhibiting extension of pannus-like synovial membrane cells in the same manner as described above. As a result, each of the lipid-bound chondroitin sulfate samples (lot Nos. 602, 602-3 and 302-2) showed almost the same extension inhibitory effect as that of the abovementioned CS-PE (lot No. 602-2). The other lipid-bound GAG compounds also showed a certain degree of extension inhibitory effect though the effect was inferior to that of CS-PE.

TEST EXAMPLE 3

Effect of lipid-bound GAG on *E. coli*-induced arthritis rabbit

A 1,000 μg portion of heat-killed *E. coli* cells were suspended in 0.5 ml of physiological saline, and the suspension was mixed with the same volume of Freund's incomplete adjuvant. A 1 ml portion of the resulting suspension was injected intramuscularly to each of 18 Japanese white rabbits (2 kg in body weight) once a month 4 times in total. On the 8th day after the final sensitization, 1 ml of a suspension of heat-killed *E. coli* cells (1,000 μg as antigen) was injected into both knee joints of each rabbit to cause arthritis. Starting immediately after the injection for causing arthritis, 1 ml of phosphate-buffered saline (to be referred to as "PBS" hereinafter), 1 ml of CS-PE(lot No. 602-2, 1 mg/ml) or 1 ml of HA-PE (lot No. 600, 1 mg/ml) was injected into the left knee joint cavity of 6 rabbits 5 to 6 times weekly. The right knee joints were remained untreated after the injection for causing arthritis to serve as controls.

After 4 or 6 weeks of the injection for causing arthritis, the experimental animals were dissected to collect joint samples. Each of the joint tissue samples was fixed with formalin, subjected to paraffin embedding and then made into HE-stained sections. The tissue specimen thus prepared from each joint part was observed under a microscope to pathologically evaluate the degree of arthritis, especially pannus extension and synovitis.

From the whole body observation, the animals which received the composition of the present invention were evidently active in comparison with those which received PBS. Further, the drug-administered left knee joints hardly showed swellings compared to the control right knee joints, thus showing improvement of arthritic symptoms.

The observation of tissue specimens revealed villous growth of synovial membrane associated with deposition of fibrin on the synovial membrane surface layer and infiltration of lymphoid follicle-like small circular cell in the tissue under the synovial membrane surface layer in all animals of the PBS-administered control group. The arthritis tissue was evidently developed into pannus which extended to the cartilage surface.

In the CS-PE-administered group, two out of the 6 animals could be compared in the left and right knee joints at the same positions. The control right knee joint of each of the two cases revealed growth of synovial membrane villi accompanied by infiltration of lymphoid follicle-like small circular cell and extension of the inflammatory glanulation tissue as pannus toward the cartilage surface layer. Comparing with the right knee joint mentioned above at the same position of the same animal, the pannus extension toward articular cartilage was found to be suppressed in the CS-PE-injected left knee joint.

In the HA-PE-administered group, the pannus extension inhibitory effect was not so clear as the case of the CS-PE-injected group, but the control right knee joint showed such a strong inflammatory symptom that fibrin deposited on the surface layer of the inflamed synovial membrane and follicle-like lymphocytes aggregated under the same surface layer. On the other hand, inflammatory symptoms were relatively mild in the HA-PE-injected left joint synovial membrane. Such an anti-inflammation effect was found in 3 out of the 6 cases.

On the basis of the above results, it is evident that the lipid-bound GAG of the present invention exhibits an effect of ameliorating RA-like arthritic symptoms.

TEST EXAMPLE 4

Lipid-bound GAG remaining in rabbit articular cartilage tissues

Normal Japanese white rabbits (body weight of 2.7 to 3.0 kg) and arthritis-induced Japanese white rabbits (body weight of 2.7 to 3.0 kg) were used as experimental animals. The arthritis-induced animals were obtained by continuously administering *E. coli* dead cells together with incomplete Freund's adjuvant to Japanese white rabbits subcutaneously for about 6 months, directly injecting *E. coli* dead cells into both knee joints of each of the thus treated rabbits and then selecting animals which showed arthritic symptoms 1 week after the injection.

Chondroitin sulfate fluorescence-labeled with fluorescein amine (to be referred to as "F-CS" hereinafter) and fluorescence-labeled CS-PE (to be referred to as "F-CS-PE" hereinafter) prepared in the same manner as above were each dissolved in PBS (1 mg/ml or 10 mg/ml), and each of the resulting solutions was subjected to sterile filtration. The thus prepared solutions to be tested were injected into knee joints of the abovementioned normal and *E. coli*-sensitized rabbits in a dose of 1 ml/joint. The experimental animals were divided into 1-mg-administered and 10 mg-administered groups (only 10 mg-administered group for the normal rabbits), and F-CS was injected into their left knee joints and F-CS-PE into their right knee joints. One day after the administration of test samples, the rabbits were sacrificed and dissected to collect knee joint tissues, as well as elbow joint tissues to be used as controls. The collected joint tissues include fat tissue-containing synovial membrane tissue, articular meniscus, cruciate ligament, epiphyseal cartilage and synovia.

Figure 1A:
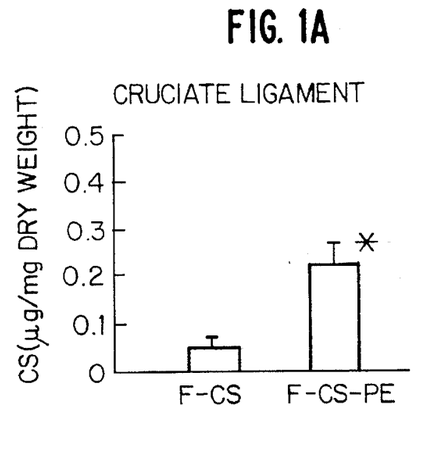
FIGS. 1A through 1E are graphs Showing the remaining amount of fluorescence-labeled chondroitin sulfate (F-CS) or fluorescence-labeled CS-PE (F-CS-PE, PE: L-($\alpha$-phosphatidyl)ethanolamine dipalmitoyl) in each tissue of a normal Japanese white rabbit to which F-CS or F-CS-PE has been administered.
Figure 1B:
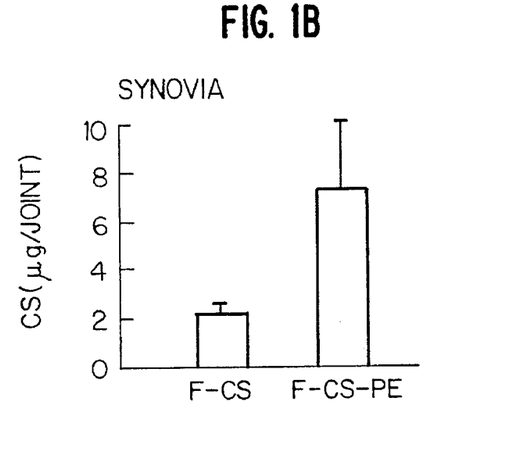
Figure 1C:
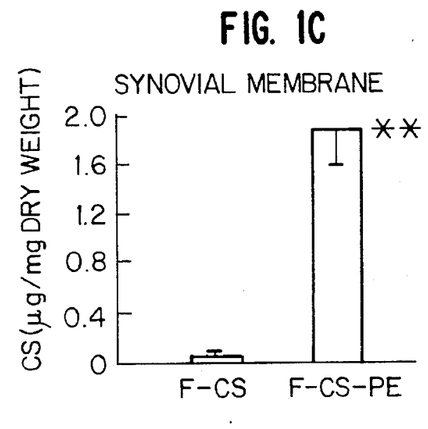
Figure 1D:
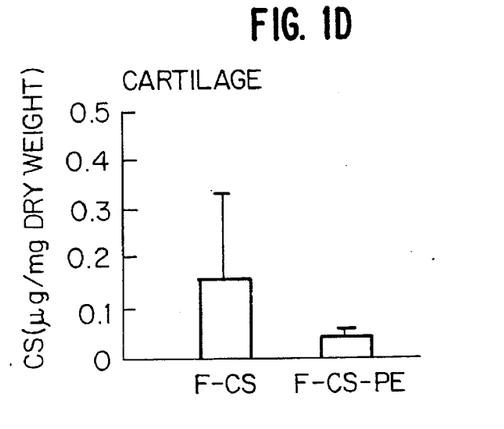
Figure 1E:
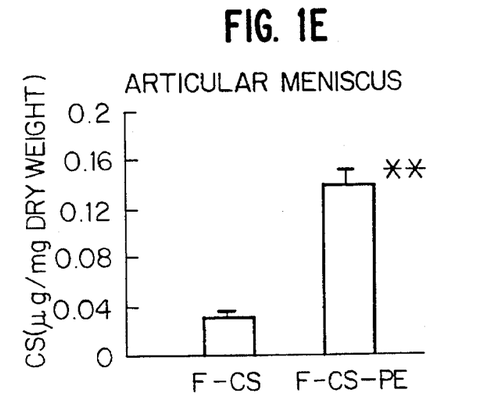
Figure 2A:
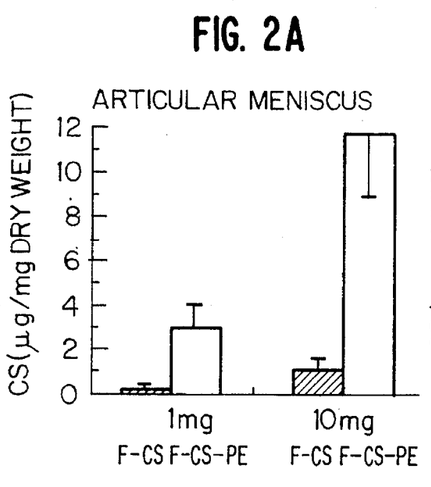
FIGS. 2A through 2D are graphs showing the remaining amount of fluorescence-labeled chondroitin sulfate (F-CS) or fluorescence-labeled CS-PE (F-CS-PE) in each tissue of a Japanese white rabbit with *E. coli*-induced arthritis, to which F-CS or F-CS-PE has been administered.
Figure 2B:
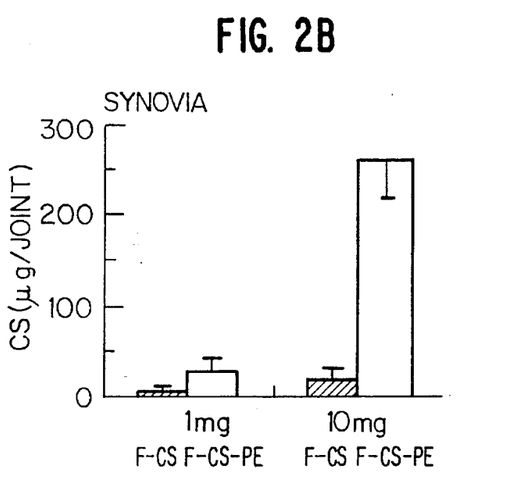
Figure 2C:
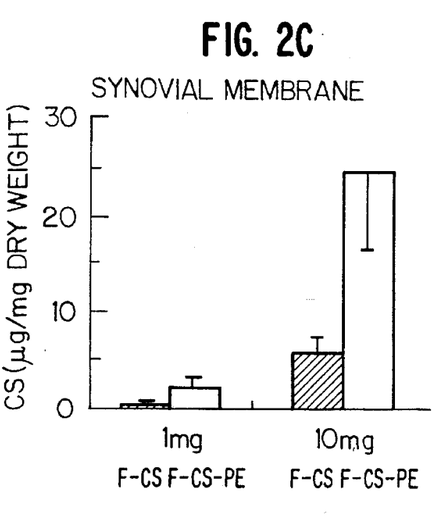
Figure 2D:
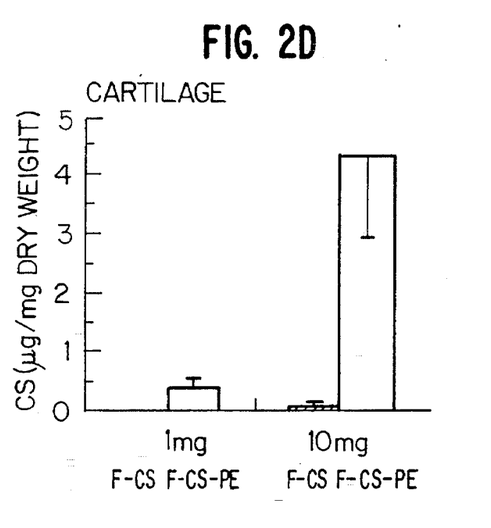
Figure 3A:
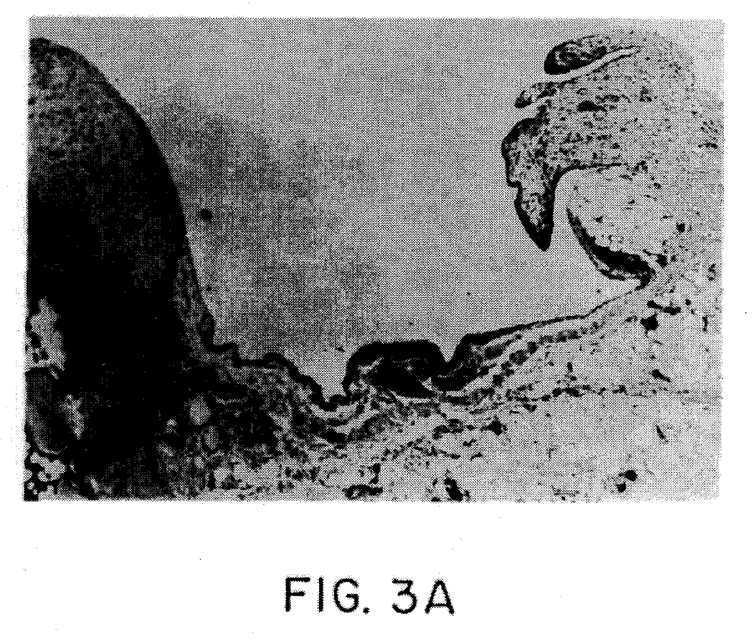
FIGS. 3A through 3E are photographs of microscopically observed joint tissue specimens derived from the groups of *E. coli*-sensitized arthritis-induced rabbits as the results of Test Example 3. Photograph Nos. 3A through 3E respectively show the respective joint tissue specimens of: the PBS-administered control group; the right: knee joint (control) of the CS-PE-administered group; the left knee joint of the CS-PE-administered group; the right knee joint (control) of the HA-PE-administered group; and the left knee joint of the HA-PE-administered group.
Figure 3B:
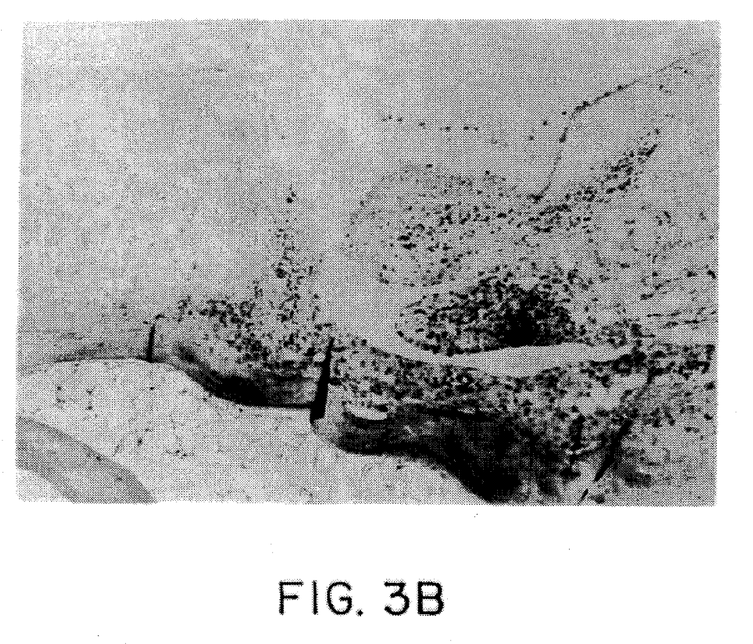
Figure 3C:
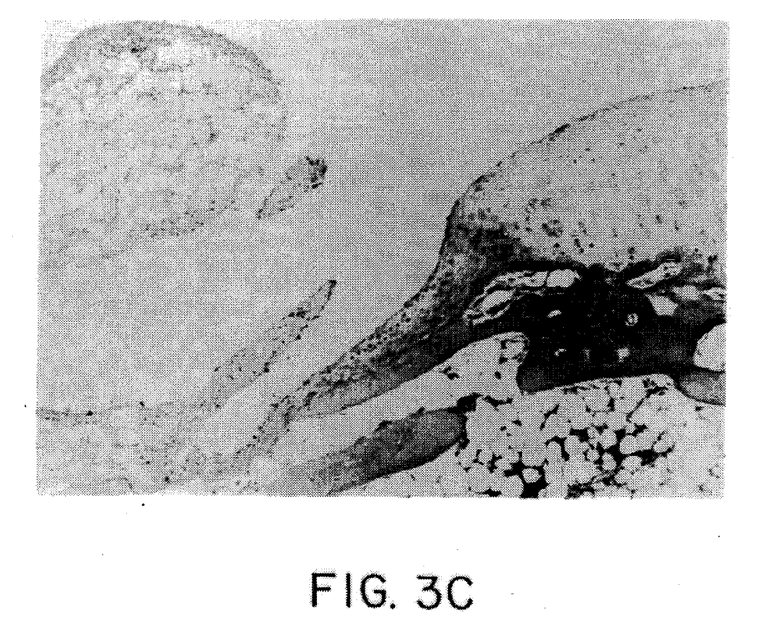
Figure 3D:
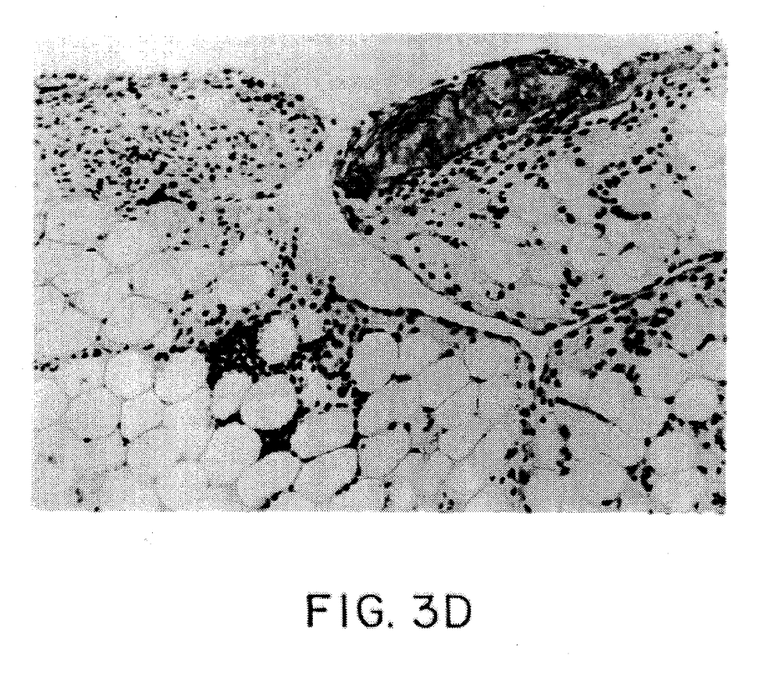
Figure 3E:
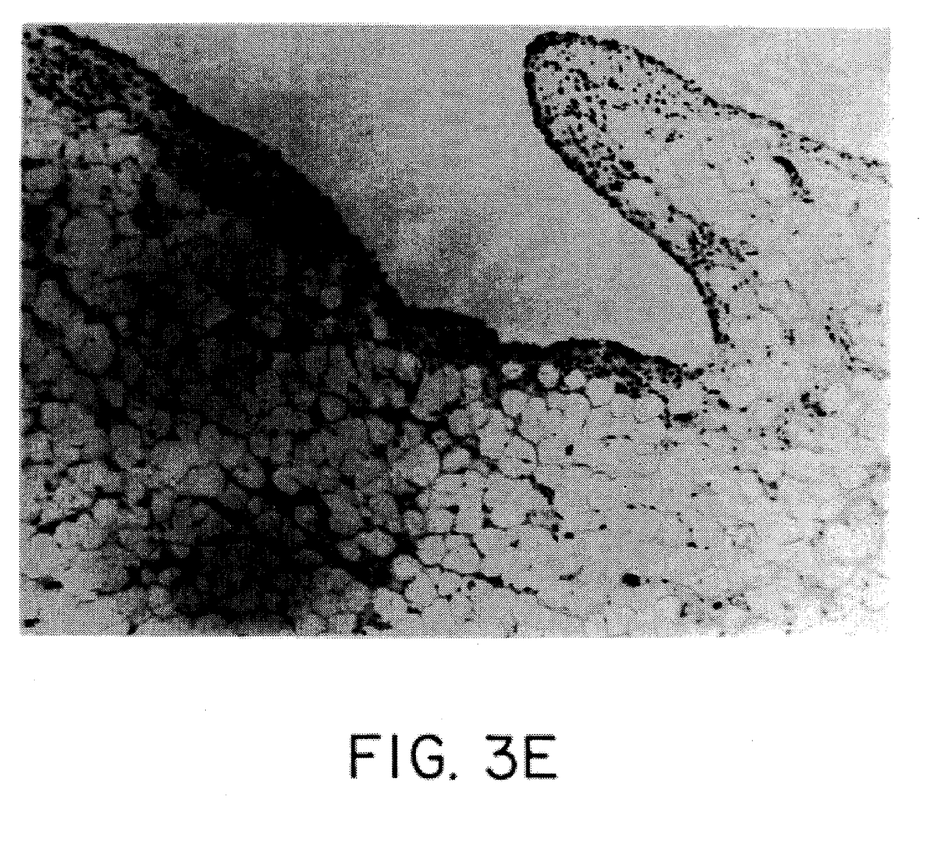

Each of the tissue samples was lyophilized and treated with Pronase (Kaken Pharmaceutical Co., Ltd.) followed by extraction. The resulting extract was checked for its fluorescence intensity to calculate the amount of the fluorescence-labeled derivative adhered to each tissue. The results obtained from the normal rabbits and the arthritis rabbits are shown in FIGS. 1 and 2, respectively.

In the case of the normal rabbits, F-CS-PE remained in the synovia in a higher amount than F-CS, but the difference between them was not significant. Also, no significant difference was found between F-CS-PE and F-CS their migration into the articular cartilage. However, migrated amounts of F-CS-PE into meniscus, cruciate ligament and synovial membrane were significantly higher than those of F-CS. Especially, F-CS-PE was detected in the synovial membrane tissue in an amount 30 times as high as F-CS. Since the synovial membrane tissue contains a large quantity of fat tissue, it seems probable that, F-CS-PE is accumulated in the fat tissue.

In the case of the joint tissues of the arthritis rabbits, F-CS-PE was incorporated into synovia, joint cartilage, meniscus and synovial membrane in an amount several to about 20 times as high as F-CS. In addition, the remaining amount increased depending on the dose (1 mg and 10 mg). Most significant differences from the normal rabbits are that the higher amounts of the test compounds were incorporated in tissues as a whole in the arthritis rabbits, and the amount of F-CS-PE remained in cartilage tissues is especially high in the inflamed joint tissues. These results seem to be related to the coating of a fibronectin-like substance and an immune complex on the surface of arthritis cartilage.

FORMULATION EXAMPLE

Solutions for intraarticular injection

A 45 mg portion of aseptically prepared CS-PE (lot No. 602-2) or HA-PE (lot No. 600) was dissolved in 45 ml (final volume) of phosphate-buffered saline (PBS) at room temperature. Each of the thus prepared solutions was subjected to sterile filtration using a membrane filter of 0.22 μm pore size, and the filtrate was dispensed in 2.5 ml aliquots into ampuls. Thus, solutions for intraarticular injection respectively containing 2.5 mg per ampul of the above active ingredients were prepared.

While the invention has been described in detail and with reference to specific examples thereof, it will be apparent to one skilled in the art that various changes and modifications can be made therein without departing from the spirit and scope thereof.

What is claimed is:

1. A method of treating rheumatism which comprises administering to mammals suffering from rheumatism a composition comprising between 0.1 to 80% lipid-bound glycosaminoglycan (gag) or a pharmaceutically acceptable salt thereof and a pharmaceutically acceptable carrier, wherein said composition is administered in a dose of 0.1 to 2,000 mg/adult once a day or within several weeks.

2. The method according to claim 1, wherein said lipid-bound glycosaminoglycan consists essentially of a lipid bound to a glycosaminoglycan via an acid amide bond, an aminoalkyl bond or an ester bond.

3. The method according to claim 1, wherein the lipid-bound glycosaminoglycan is obtained by oxidizing a reducing terminal of a glycosaminoglycan to cleave the reducing terminal, lactonizing the cleaved product and reacting the resulting lactone compound with a primary amino group of a lipid.

4. The method according to claim 1, wherein the lipid moiety of said lipid-bound glycosaminoglycan is a glycerolipid and the glycosaminoglycan moiety thereof is chondroitin sulfate, dermatan sulfate or hyaluronic acid.

5. The method according to claim 4, wherein the glycerolipid is a glycerophospholipid or acylglycerol.

6. The method according to claim 5, wherein the glycerophospholipid is phosphatidylethanolamine or phosphatidylserine.

7. The method according to claim 1, wherein said composition is in the form of intraarticularly injectable solution.

8. The method according to claim 1, wherein said method comprises topically administering the composition to rheumatoid arthritis sites.

9. The method according to claim 8, wherein the method comprises administering a therapeutically effective amount of the lipid-bound glycosaminoglycan to prevent the extension of pannus.

* * * * *